United States Patent [19]

Fishler et al.

[11] Patent Number: 5,072,028

[45] Date of Patent: Dec. 10, 1991

[54] PROCESS FOR THE PREPARATION OF BROMO-SUBSTITUTED AROMATIC ESTERS OF α, β-UNSATURATED ACIDS

[75] Inventors: Theodor-Morel Fishler, Haifa; Michael Peled, Beer-Sheva; Leonard M. Shorr, Haifa, all of Israel

[73] Assignee: Bromine Compounds Limited, Beer-Sheva, Israel

[21] Appl. No.: 500,679

[22] Filed: Mar. 28, 1990

[30] Foreign Application Priority Data

Mar. 29, 1989 [IL] Israel .......................................... 89791

[51] Int. Cl.⁵ ............................................ C07C 69/052
[52] U.S. Cl. ..................................................... 560/221
[58] Field of Search ........................................ 560/221

[56] References Cited
FOREIGN PATENT DOCUMENTS 2508468 9/1976 Fed. Rep. of Germany .
2543722 4/1977 Fed. Rep. of Germany .

Primary Examiner—Paul J. Killos

Attorney, Agent, or Firm—Michael N. Meller

[57] ABSTRACT

A process for the preparation of bromo-substituted aromatic esters of α, β-unsaturated acids of the formula

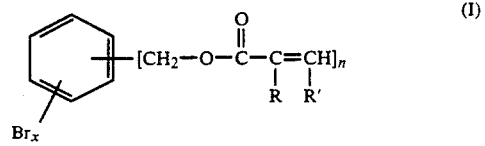

wherein
n is 1 or 2,
x = 6'n, and
R and R' are hydrogen or alkyl;

comprises reacting a salt of α,β-unsaturated acid and an alkali with a bromo-substituted benzyl halide in an inert substantially water-immiscible solvent and in the presence of a phase-transfer catalyst.

19 Claims, No Drawings

PROCESS FOR THE PREPARATION OF BROMO-SUBSTITUTED AROMATIC ESTERS OF α, β-UNSATURATED ACIDS

FIELD OF THE INVENTION

The present invention relates to a process for the preparation of bromo-substituted aromatic esters of α,β-unsaturated acids. More particularly the invention relates to a process for the preparation of esters of the formula:

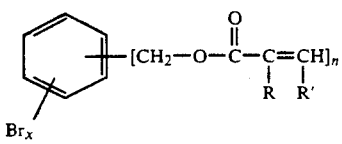

wherein:
n is 1 or 2,
x = 6-n, and
R and R' are hydrogen or alkyl.

BACKGROUND OF THE INVENTION

Acrylates encompassed by formula I, in which R' is hydrogen, are useful intermediates for the preparation of polymeric flame retardant agents (e.g., U.S. Pat. No. 4,128,709), but they may be useful as monomeric flame-retardant agents for certain applications, as described, e.g., in the copending Israeli Patent Application No. 86604 of the same applicant.

THE PRIOR ART

The preparation of such acrylates is described in U.S. Pat. No. 4,059,618, and it involves reacting acrylic acid with the appropriate bromobenzyl chloride in polar solvents which are miscible to at least some degree with water, such as ethylene glycol monomethyl ether or methyl glycol. In the process described in this patent it is necessary to add a polymerization inhibitor, because polymerization takes place during the esterification reaction.

SUMMARY OF THE INVENTION

It has now surprisingly been found, and this is an object of the invention, that it is possible to provide a process for the preparation of compounds of formula I which is free from the danger of undesired polymerization, and which therefore does not require the use of polymerization inhibitors. As will be apparent to a person skilled in the art the ability to dispense with the inhibitors is a considerable process advantage, reduces the need for precise monitoring of reagent concentrations to avoid the neutralization of the inhibitor by the presence of alkali, which may lead to premature polymerization, and avoids problems associated with inhibitor removal and traces of inhibitor left in the product.

It is a further object of the invention to provide a process which permits to obtain a product i. high yields.

The processes of the art afford relatively low yields, which are much lower than those obtained with the process of the invention. U.S. Pat. No. 4,059,618, for instance, prepared tetrabromo-p-xylylenebisacrylate with 79% yield, pentabromobenzyl acrylate with 66% yield, and pentabromobenzyl methacrylate with 52% yield, while with the process of the invention the yields for these products are 82%, >90% and 90% respectively.

The monomers obtained according to the process of the invention also form part of the present invention. Of particular interest is the monomer pentabromobenzyl monoacrylate, which has been shown by the applicant to possess outstanding flame-retardant properties. Providing this monomer in high yield is advantageous also when it is desired to use it as an intermediate for the preparation of the well-known flame retardant material polypentabromobenzyl acrylate, as will be apparent to the skilled chemist.

The process according to the invention comprises reacting a salt of an α,β-unsaturated acid and an alkali with a bromo-substituted benzyl halide in an inert, water-immiscible solvent and in the presence of a phase-transfer catalyst.

Preferably the inert solvent is a substantially water-immiscible hydrocarbon and/or halocarbon, such as chlorobenzene, toluene, methylene chloride, chlorobromomethane, dibromomethane, mixtures of methylene chloride, chlorobromomethane and dibromomethane, ethylene dichloride and ethylene dibromide, and the alkali is a metal hydroxide, preferably NaOH, KOH or carbonates thereof.

The phase-transfer catalyst can be a conventional phase-transfer catalyst, such as a quaternary ammonium salt, for example Aliquat 336 (tricaprylylmethyl ammonium chloride), hexadecyltrimethyl ammonium chloride or tetrabutyl ammonium bromide.

The molar ratio of the acid to PBB-Br may be between 1:1 and 1.8:1, preferably between 1.05:1 and 1.2:1. The concentrations of reagents are such as to produce, at full conversion, a product concentration of 25-55%, preferably between 30% and 40%.

The salts, such as NaBr and KBr formed in the reaction can be removed by hot filtration, and the product can then be precipitated by cooling the reaction mixture and recovered.

As will be apparent to the skilled chemist, the process of the invention presents a further important advantage, viz., that the mother liquor can be recycled and used for subsequent batches. By operating with recycle, only a make-up of phase-transfer catalyst and of solvent is needed, and the unreacted bromobenzyl halide remaining in the mother liquor is recycled and used, thereby improving the yield of the product.

The product is thus obtained in a high purity and is useful as such in fire retardant applications. If higher purities are required, as in some copolymerization applications, the product may be further purified by recrystallization.

As stated, replacing the solvents described in U.S. Pat. No. 4,059,610 with the solvents of the present invention has the surprising result that no polymerization takes place, even in the total absence of a polymerization inhibitor, with the advantages resulting from this fact.

All the above and other characteristics and advantages of the invention will be better understood through the following illustrative and non-limitative examples.

EXAMPLE 1

Preparation of Pentabromobenzyl acrylate

To a 500 ml three-necked flask equipped with mechanical stirrer, thermometer and a condenser there are added 290 ml of chlorobenzene, 8.3 gr. NaOH (0.21 mole), and 15 gr. acrylic acid (0.21 mole) were added in small portions. The mixture was heated during 30 minutes at 30°-50° C., to give the sodium salt of acrylic acid. After this period, 112 gr. of pentabromobenzylbromide (PBB-Br) (0.2 mole) were added, as well as 1.3 gr. of Aliquate-336 (ex Henkel). The mixture was then heated to about 80°-100° C. under vigorous stirring. The reaction continued for about 4 hours, and reaction completion was monitored by analyzing for PBB-Br by GC or HPLC.

After completion of the reaction, the mixture was cooled to 60° C. and NaBr which formed in the reaction was filtered out. The remaining mixture was then cooled to 0°-5° C. The product crystallized, was filtered out, and dried to constant weight.

A white solid (m.p. 112°-115° C.) was obtained. The weight of product was 107 gr., corresponding to a 96% yield based on PBB-Br. The melting point of the product, after recrystallization from toluene or chlorobenzene or methylethyl ketone was 122°-123° C. Purity (HPLC) was 95-97 wt %. N.M.R. ($CDCl_3$): 5.7 (S, 2H); 5.8 (M, 1H); 6.1 (M, 1H); 6.4 (M, 1H).

EXAMPLE 2

Preparation of Pentabromobenzyl methacrylate

Operating as in Example 1, but using methacrylic acid, a white powder was obtained in 90% yield (based on PBB-Br). M.P. 153°-155° C., HPLC (area %)-99%. % Br: Calcd.—70.0%; found—70.8%. N.M.R. ($CDCl_3$): 5.6 (S,2H); 5.6 (M, 1H); 6.1 (M, 1H); 1.9 (S,3H).

EXAMPLE 3

Preparation of Tetrabromo-p-xylidene diacrylate

To a 250 ml three-necked flask, equipped with a mechanical stirrer, a condenser and a thermometer there were added 80 gr. of toluene, 5 gr. KOH (95%, 0.09M), and 6.2 gr. acrylic acid (0.09 mole). The mixture is stirred for about half an hour at 30° C. to obtain the potassium salt of acrylic acid.

After this period there are added 20 gr. (0.035M) of tetrabromo-pxylidene dibromide (p-TBX-2Br) and 0.5 gr. Aliquat 336, and the mixture is heated to 80° C. until p-TBX-2Br disappears, as monitored by TLC. The reaction is completed in about 2 hours, after which the mixture is cooled to about 60° C. and KBr is filtered off. The remaining mixture is cooled to about 0° C. overnight, and then filtered to give 16 g of product, with 82% yield (based on p-TBX-2Br).

M.P.=158°-161° C. Purity (HPLC)=93%. N.M.R. ($CDCl_3$): 5.9 (M, 2H); 6.1 (M, 2H); 6.5 (M, 2H); 5.7 (S, 4H).

EXAMPLE 4

Preparation of tetrabromo-p-xylidene dimethacrylate

Operating as in Example 3, but using methacrylic acid instead of acrylic acid, the title product is obtained with 91% yield. M.P. =158°-160° C. % Br: Calcd=54.2%; found=55.7%. HPLC (area %)=99%. N.M.R. ($CDCl_3$): 5.6 (M, 2H); 5.6 (S, 4H); 6.1 (M, 2H); 2.0 (S, 6H).

EXAMPLE 5

Preparation of Tetrabromo-o-xylidene diacrylate

Operating as in Example 3, but using the ortho instead of the para isomer, the title compound was obtained in 52% yield. M.P.=103°-105° C. N.M.R. ($CDCl_3$): 5.8 (M, 2H); 6.1 (M, 2H); 6.4 (M, 2H); 5.5 (S, 4H).

EXAMPLE 6

Preparation of Tetrabromo-o-xylidene dimethacrylate

Operating as in Example 4, but using the ortho instead of the para isomer, the title compound was obtained with 76% yield. M.P.=70°-72° C. N.M.R. ($CDCl_3$): 5.5 (S, 4H); 5.6 (M, 2H); 6.1 (M, 2H); 1.9 (S, 6H).

EXAMPLE 7

Preparation of Pentabromobenzyl acrylate with recycle

A 500 ml three-necked flask provided with a mechanical stirrer, a thermometer and a condenser is filled with 292 ml solvent. 8.33 g NaOH is added. Next 15.0 g acrylic acid is added in portions. During the neutralisation (±30 min) the temperature is kept <30° C. In the first batch 112 g PBB-Br and 1.3 g aliquat 336 in 12.4 g chlorobenzene (=10% aliquat solution) are added. From batch 2 onward (using chlorobenzene mother liquor from a previous batch with a make up of fresh chlorobenzene) 109.8 g PBB-Br and 3 g 10% aliquat solution are used. This is due to the fact that unreacted PBB-Br (<2%) is recycled with the mother liquor. In the mother liquor 70-80% of the catalyst is found back. When the aliquat is added the mixture is heated to 100° C. and kept there for 4 hours. When less than 2% PBB-Br (GC area %) is found in the reaction mixture, the mixture is cooled to 60° C. At this temperature the sodium salts are removed from the mixture by way of a hot filtration. The filtrate is cooled to 0°-5° C. in order to precipitate as much PBB-MA as possible. Since PBB-MA is extremely soluble in chlorobenzene the cooling is very important. The product is filtered at 0°-5° C. The sodium salts, which are removed from the mixture in the hot filtration, are washed with fresh chlorobenzene. This chlorobenzene wash is used as make up in the next batch of PBB-MA.

EXAMPLE 8

Preparation of Pentabromobenzyl acrylate with a carbonate

In a 1000 ml stirred reactor there were added 738 g of a chlorobenzene solution recycled from a previous run and 30 g anhydrous $K_2CO_3$. The mixture was stirred vigorously in order to disperse the solid and over it there were added, dropwise from a dropping funnel, 31 g of acrylic acid. Upon completion of the reaction, as seen by cessation of gas evolution and foaming, 205 g of PBB-Br, 4.9 g of 45.5% NaOH aqueous solution and 0.5 g Aliquat 336 were added and the heating started. The temperature was maintained at 75° C. After 1.5-2 hours the reaction ended, as proved by the absence, or less than 2% presence, of PBB-Br (GC). The mixture was filtered at the reaction temperature, and the filtrate was subjected to careful cooling to 0°-5° C., at which temperature the PBB-MA crystallizes out and can be easily filtered. The material was of high purity and did not require any further washing. The product had the same properties as in Example 1, and the yield was more than 90%.

EXAMPLE 9

Use of Tetrabutylammmonium bromide

Example 1 was repeated, using equivalent amounts of tetrabutylammonium bromide instead of Aliquat 336. Comparable results were obtained.

EXAMPLE 10

Preparation of the ester of crotonic acid

To a three-necked 250 ml flask there were added 130 ml toluene, 5 g KOH 95% (86 mmol) and 7.4 g (86 mmol) of crotonic acid. The mixture was stirred during about 30 minutes at room temperature, to obtain the salt. After this period, 40 g PBB-Br (70 mmol) and 1 g tetrabutylammonium bromide were added. The mixture was stirred during about two hours at about 70° C., until PBB-Br was no longer detectable by GC. The reaction mixture was filtered hot to remove KBr and then cooled to precipitate the product, filtered, the solid was washed with water and dried.

38 g of product were obtained in 92% yield (based on PBB-Br). M.P.=149°-151° C. NMR (CDCl$_3$): 7.0 (H,M); 5.8 (H,M), 5.64 (2H,S); 1.90 (3H,d).

EXAMPLE 11

Operating as in Example 1, the reaction mixture contained 890 ml chlorobromomethane (CBM), 47.88 g (0.84 mol) KOH, 63.5 g (0.88 mol) of Acrylic acid, 396.2 g (0.7 mol) of PBB-Br and 8.0 g of Aliquat 336 in 30 ml solution.

After 2.5 hours of reaction and work-up as in Example 1, 365 g of product, 86 wt % PBB-MA were obtained. HPLC of product area % PBB-OH 2.1, PBB-MA 87, PBB-Br 1.1. The yield of PBB-MA was 63%.

The filtrate (1518 g) yielded after evaporation 140.2 g of residual PBB-MA. Total yield of PBB-MA=91%.

EXAMPLE 12

Example 11 was repeated, using the following solvents instead of CBM: MC, CBM, a 1:1:1 mixture of MC, CBM and DBM, EDC, EDB. In all cases comparable results were obtained.

We claim:

1. A process for the preparation of bromo-substituted aromatic esters of $\alpha,\beta$-unsaturated acids of the formula

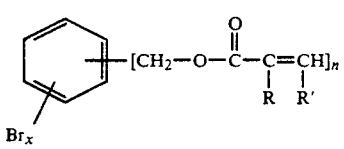

wherein:
n is 1 or 2,
x=6-n, and
R and R' are hydrogen or alkyl;
comprising reacting a salt of an $\alpha,\beta$-unsaturated acid and an alkali with a bromo-substituted benzyl halide in an inert substantially water-immiscible solvent and in the presence of a phase-transfer catalyst.

2. A process according to claim 1, wherein the solvent is selected from the group consisting of chlorobenzene, toluene, methylene chloride, chlorobromomethane, dibromomethane, mixtures of methylene chloride, chlorobromomethane and dibromomethane, ethylene dichloride and ethylene dibromide.

3. A process according to claim 1, wherein the alkali is a metal hydroxide selected from the group consisting of NaOH or KOH, or a carbonate thereof.

4. A process according to claim 1, wherein the phase-transfer catalyst is a quaternary ammonium salt.

5. A process according to claim 1, wherein the catalyst is tricaprylylmethyl ammonium chloride, hexadecyltrimethyl ammonium chloride or tetrabutyl ammonium bromide.

6. A process according to claim 1, wherein the solvent comprises mother liquor recycled from a previous reaction run.

7. A process according to claim 1, wherein the bromo-substituted benzyl halide is pentabromobenzylbromide or o- or p-tetrabromoxylidene dibromide.

8. A process according to claim 1, wherein the $\alpha$,$\beta$-unsaturated acid is acrylic, crotonic or methacrylic acid, and the resulting ester is a bromo-substituted aromatic acrylate.

9. A process according claim 8, wherein the bromo-substituted aromatic acrylate is selected from the group consisting of pentabromobenzyl acrylate, pentabromobenzyl methacrylate, tetrabromo-p-xylidene diacrylate, tetrabromo-o-xylidene diacrylate, tetrabromo-p-xylidene dimethacrylate, tetrabromo-o-xylidene dimethacrylate and pentabromobenzyl crotonate.

10. A process according to claim 2, wherein the alkali is a metal hydroxide selected from the group consisting of NaOH or KOH, or a carbonate thereof.

11. A process according to claim 2, wherein the phase-transfer catalyst is a quaternary ammonium salt.

12. A process according to claim 3, wherein the phase-transfer catalyst is a quaternary ammonium salt.

13. A process according to claim 2, wherein the solvent comprises mother liquor recycled from a previus reaction run.

14. A process according to claim 2, wherein the bromo-substituted benzyl halide is pentabromobenzylbromide or o- or p-tetrabromoxylidene dibromide.

15. A process according to claim 5, wherein the bromo-substituted benzyl halide is pentabromobenzylbromide or o- or p-tetrabromoxylidene dibromide.

16. A process according to claim 14, wherein the $\alpha,\beta$-unsaturated acid is acrylic, crotonic or methacrylic acid, and the resulting ester is a bromo-substituted aromatic acrylate.

17. A process according to claim 15, wherein the $\alpha,\beta$-unsaturated acid is acrylic, crotonic or methacrylic acid, and the resulting ester is a bromo-substituted aromatic acrylate.

18. A process according to claim 16, wherein the bromo-substituted aromatic acrylate is selected from the group consisting of pentabromobenzyl acrylate, pentabromobenzyl methacrylate, tetrabromo-p-xylidene diacrylate, tetrabromo-o-xylidene diacrylate, tetrabromo-p-xylidene dimethacrylate, tetrabromo-o-xylidene dimethacrylate and pentabromobenzyl crotonate.

19. A process according to claim 17, wherein the bromo-substituted aromatic acrylate is selected from the group consisting of pentabromobenzyl acrylate, pentabromobenzyl methacrylate, tetrabromo-p-xylidene diacrylate, tetrabromo-o-xylidene diacrylate, tetrabromo-p-xylidene dimethacrylate, tetrabromo-o-xylidene dimethacrylate and pentabromobenzyl crotonate.

* * * * *